United States Patent [19]

Dreikorn et al.

[11] Patent Number: 5,227,387
[45] Date of Patent: Jul. 13, 1993

[54] QUINOLINE NEMATICIDAL METHOD

[75] Inventors: Barry A. Dreikorn, Oxfordshire, England; Ronnie G. Edie, Greenfield, Ind.; Ronald E. Hackler, Indianapolis, Ind.; Glen P. Jourdan, Morristown, Ind.; Eriks V. Krumkalns, Indianapolis, Ind.; Robert G. Suhr, Greenfield, Ind.

[73] Assignee: DowElanco, Indianapolis, Ind.

[21] Appl. No.: 753,507

[22] Filed: Sep. 3, 1991

[51] Int. Cl.$^5$ ............................................. A01N 43/42
[52] U.S. Cl. ..................................... 514/312; 514/63; 514/249; 514/257; 514/259; 514/260; 514/311; 514/313; 546/14; 546/153; 546/159
[58] Field of Search ........................ 514/312, 313, 63

[56] References Cited

U.S. PATENT DOCUMENTS

| | | | |
|---|---|---|---|
| 5,034,393 | 7/1991 | Hackler et al. | 514/258 |
| 5,114,939 | 5/1992 | Dreikorn et al. | 514/513 |
| 5,137,879 | 7/1992 | Edie et al. | 514/63 |
| 5,145,843 | 8/1992 | Arnold et al. | 514/312 |

FOREIGN PATENT DOCUMENTS

| | | |
|---|---|---|
| 326329 | 8/1989 | European Pat. Off. |
| 0326330 | 8/1989 | European Pat. Off. |
| 326331 | 8/1989 | European Pat. Off. |
| 452002 | 10/1991 | European Pat. Off. |

OTHER PUBLICATIONS

Dreikorn et al. Chem Abstr. vol. 112, entry 55630s abstracting EP 326331 (1989).
Singh et al. Jour. Med. Chem. vol. 14, pp. 283-286 (1971).
Renault et al. Chemie Therapeuticque, 1966, pp. 339-346.

Primary Examiner—Donald G. Daus
Attorney, Agent, or Firm—Donald R. Stuart

[57] ABSTRACT

A method of inhibiting a nematode population which comprises applying to the locus of a nematode, a nematode inactivating amount of a compound of the formula (1):

$$\text{Het}-\text{X}-\text{CH}_2-\text{CH}_2-\text{Ar} \qquad (1)$$

or an N-oxide or salt thereof, wherein
Het is a nitrogen containing heterocycle, for example 8-fluoroquinazolin-4-yl, or quinoline-4-amine,
X is O, NH, or $CH_2$; and
Ar is a substituted phenyl group, for example 4-(2,2,2-trifluoroethoxy)phenyl.

20 Claims, No Drawings

QUINOLINE NEMATICIDAL METHOD

FIELD OF THE INVENTION

This invention provides a new nematicidal method. There is an acute need for new nematicides and new nematicidal methods, because available nematicides typically have high mammalian toxicity and must be used at high rates. A nematicide that can be applied at lower rates and that has lower mammalian toxicity would represent a significant advance.

SUMMARY OF THE INVENTION

More specifically, this invention provides a method of inhibiting a nematode population which comprises applying to the locus of a nematode, a nematode inactivating amount of a compound of the formula (1):

Het—X—CH$_2$—CH$_2$—Ar   (1)

or an N-oxide or salt thereof, wherein
Het is a group selected from:

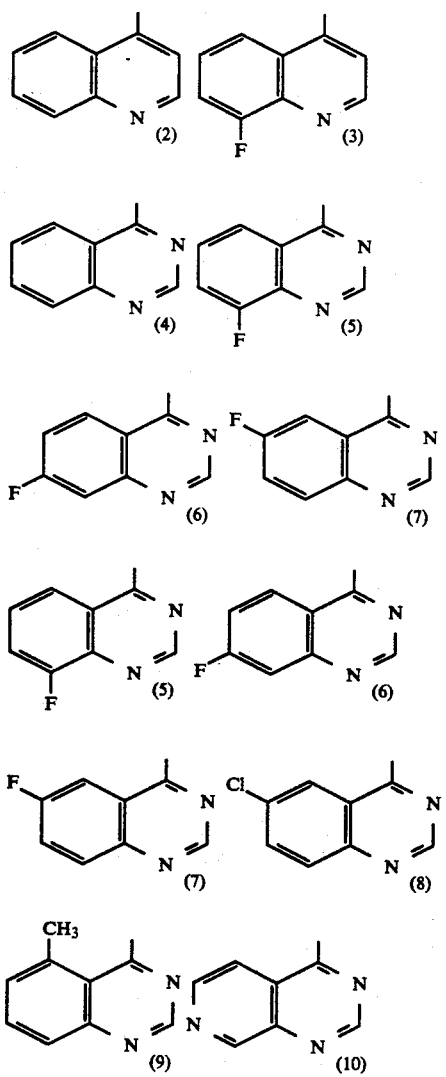

-continued

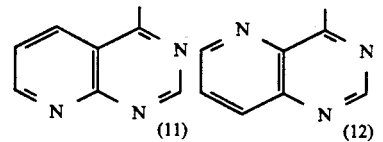

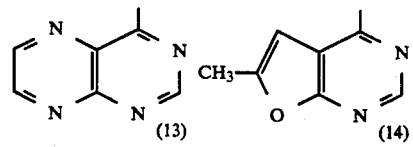

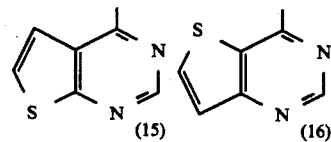

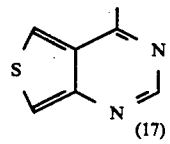

X is O, NH, or CH$_2$;
Ar is a substituted phenyl group of formula (18), (19), or (20)

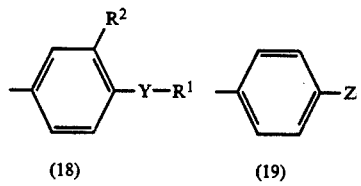

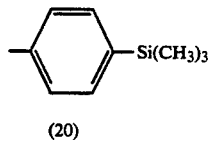

wherein
Y is O or S;
R$^1$ is (C$_2$-C$_5$) alkyl, (C$_3$-C$_7$) branched alkyl, halo (C$_1$-C$_4$) alkyl, phenyl, or phenyl substituted with CF$_3$, CN or halo;
R$^2$ is H, F, or Cl, or R$^2$ combines with Y—R$^1$ to form —CH$_2$—CH$_2$—O— or —O—CF$_2$—O—; and
Z is halo.

DETAILED DESCRIPTION OF THE INVENTION

Throughout this document, all temperatures are given in degrees Celcius, and all percentages are weight percentages unless otherwise stated.

The term "halo" refers to a F, Cl, Br, or I atom.

The term "haloalkyl" refers to straight chain and branched chain groups.

The term "HPLC" refers to a high pressure liquid chromatography.

The term "inhibiting a nematode" refers to a decrease in the numbers of living nematodes.

The term "nematode-inactivating amount" is used to describe the amount, which is sufficient to cause a measurable reduction in the treated nematode population.

The term "peanut root knot nematode assay" refers to the test method described in detail hereinafter.

PREFERED EMBODIMENTS

While the compounds of formula (1) as a class are exceptionally active as nematicides, use of certain subclasses of these compounds is preferred for reasons of greater efficacy. More specifically, use of the following subclasses of compounds is preferred:

a) compounds of formula (1) that provide at least 80% control when tested in the peanut root knot nematode assay at 12 ppm;
b) compounds of formula (1) wherein Het is a quinoline group of formula (2);
c) compounds of formula (1) wherein Het is an 8-fluoroquinoline group of formula (3);
d) compounds of formula (1) wherein Het is a quinazoline group of formula (4);
e) compounds of formula (1) wherein Het is an 8-fluoroquinazoline group of formula (5);
f) compounds of formula (1) wherein the Ar group is a substituted phenyl group of formula (18) wherein $R^1$ is halo($C_1$–$C_4$)alkyl;
g) compounds of formula (1) wherein the Ar group is a substituted phenyl group of formula (18) wherein $R^1$ is selected from $CF_3$, $CHF_2$, $CF_2CF_3$, $CH_2CF_3$, $CF_2CHF_2$, $CH(CH_3)CF_3$, $CH_2CF_2CF_2H$, and $CH_2CF_2CF_3$;
h) compounds of formula (1) wherein the Ar group is a substituted phenyl group of formula (18) wherein $R^1$ is a ($C_3$–$C_6$) branched alkyl group;
i) compounds of formula (1) wherein the Ar group is a substituted phenyl group of formula (18) wherein $R^1$ is a phenyl group that is substituted with one or more halo or $CF_3$ groups;
j) compounds of formula (1) wherein the Ar group is a substituted phenyl group of formula (18) wherein $R^1$ is ($C_2$–$C_5$) alkyl.

Use of the following compounds is particularly preferred due to their extraordinary activity Each was found to give 100% control when tested at a concentration of about 1 ppm in the soil against the peanut root knot nematode.

8-fluoro-4-[2-[4-(difluoromethoxy)phenyl]ethoxy]-quinazoline;
8-fluoro-4-[2-[4-(pentafluoroethoxy)phenyl]ethoxy]-quinoline;
4-[2-[4-(2,2,2-trifluoroethoxy)phenyl]ethoxy]quinazoline;
8-fluoro-4-[2-[4-(2,2,2-trifluoroethoxy)phenyl]ethoxy]-quinazoline;
8-fluoro-4-[2-[4-[4-(trifluromethyl)phenoxy]phenyl]ethoxy]-quinazoline;
8-fluoro-4-[2-(4-n-pentoxyphenyl)ethoxy]quinazoline;
8-fluoro-N-[2-[4-(2,2,2-trifluoroethoxy)phenyl]ethyl]-quazoline-4-amine;
8-fluoro-4-[2-[4-(trifluoromethoxy)phenyl]ethoxy]-quinazoline;
4-[2-[4-(4-fluorophenoxy)phenyl]ethoxy]quinazoline;
8-fluoro-4-[2-[4-(t-butoxy)phenyl]ethoxy]quinoline;
N-[2-[4-(2,2,2-trifluoroethoxy)phenyl]ethyl]quinazolin-4-amine;
5-methyl-N-[2-[4-(trifluoromethyl)phenyl]ethyl]-quinazolin-4-amine;
N-[2-[3-fluoro-4-(2,2,2-trifluoroethoxy)phenyl]ethyl]-quazolin-4-amine;
8-fluoro-4-[2-[3-fluoro-4-(2,2,2-trifluoroethoxy)phenyl]ethoxy]quinoline;
6-chloro-N-[2-[4-(2,2,2-trifluoroethoxy)phenyl]ethyl]-quinazolin-4-amine;
4-[2-[4-[4-(trifluromethyl)phenoxy]phenyl]ethoxy]-pyrido-[2,3-d]pyrimidine.

Other preferred compounds include 4-[2-[4-(4- and 8-fluoro-4-[2-[4-chlorophenoxy)phenyl]ethoxy]-quinazoline. (4-chlorophenoxy)phenyl]ethoxy]quinazoline.

The following table identifies specific compounds of formula (1) wherein Ar is a group of formula (18) or (20) and gives the results of testing them against the peanut root knot nematode, Meloidogyne arenaria, in the peanut root knot nematode assay. The peanut root knot nematode assay is carried out as follows. Each test compound is initially formulated as a 400 ppm solution by combining 19.2 mL of 0.05% solution of Tween 20 (polyoxyethylene (20) sorbitan monolaurate) in water with a solution of 8 mg of the compound in 0.8 mL of acetone/EtOH (9/1). The 400 ppm solution is then diluted with water to give a 200 ppm solution Three to four cucumber seeds are placed in 16 g of clean white sand, and 1 mL of the 200 ppm solution of test compound is added. This provides a concentration of the compound in the soil of 12 ppm. The cups are allowed to dry one to two hours, and then one mL of a concentrated (50 to 60 per mL) nematode (Meloidogyne arenaria) suspension is added to each cup. The cups are incubated for four to seven days. Then 11 mL of deionized water is added to each cup and the cup is gently shaken to rinse the nematodes from the sand. The suspension is poured into a watchglass and observed under a dissecting microscope at 15×–20×. An activity rating is given based on nematode mortality. Aldicarb, carbofuran, and fenamiphos are used as chemical standard compounds. Results are reported in the last column of the following table.

| Example No. | Het | X | Y | $R^1$ | $R^2$ | MP °C. | Nematode Results at 12 ppm % control |
|---|---|---|---|---|---|---|---|
| 1 | 2 | O | O | 1,1,2,2-tetrafluoroethyl | H | 70–72 | 0 |
| 2 | 2 | O | O | 2,2,2-trifluoroethyl | H | 65–66 | 100 |
|   |   |   |   |   |   |   | 100 |
| 3 | 2 | O | O | ethyl | H | 65–66 | 100 |
|   |   |   |   |   |   |   | 100 |
|   |   |   |   |   |   |   | 100 |
|   |   |   |   |   |   |   | 87.5 |
| 4 | 2 | O | O | t-butyl | H | oil | 100 |
| 5 | 2 | O | O | 1,1-dimethylpropyl | H | oil | 100 |
|   |   |   |   |   |   |   | 90 |

-continued

| Example No. | Het | X | Y | R¹ | R² | MP °C. | Nematode Results at 12 ppm % control |
|---|---|---|---|---|---|---|---|
| 6 | 2 | O | O | 1-ethyl-1-methylpropyl | H | oil | 100 |
| 7 | 3 | O | O | 4-chlorophenyl | H | 130 | 100 |
| 8 | 2 | NH | O | ethyl | H | 125–126 | 0 |
| 9 | 3 | O | O | 1,1,2,2-tetrafluoroethyl | H | 70–72 | 100 |
| | | | | | | | 99.5 |
| | | | | | | | 70 |
| 10 | 3 | O | O | difluoromethyl | H | 114 | 100 |
| | | | | | | | 0 |
| | | | | | | | 90 |
| 11 | 3 | O | O | pentafluoroethyl | H | 92.5 | 100 |
| | | | | | | | 100 |
| 12 | 3 | O | O | 2,2,2-trifluoroethyl | H | 119 | 100 |
| | | | | | | | 100 |
| 13 | 3 | O | O | trifluoromethyl | H | 87–89 | 100 |
| 14 | 3 | O | O | 2,2,3,3-tetrafluoropropyl | H | 75 | |
| 15 | 3 | O | O | 2,2,2-trifluoroethyl | F | 47–49 | 100 |
| 16 | 3 | O | O | 1-methylethyl | H | 111–113 | 0 |
| 17 | 3 | O | O | n-butyl | H | 80–82 | 100 |
| 18 | 3 | O | O | t-butyl | H | 97–98 | 100 |
| | | | | | | | 100 |
| | | | | | | | 100 |
| 19 | 3 | O | O | 1,1-dimethylpropyl | H | oil | 100 |
| | | | | | | | 100 |
| 20 | 3 | O | O | 1-ethyl-1-methylpropyl | H | oil | 100 |
| | | | | | | | 50 |
| 21 | 3 | O | O | —CH₂—CH₂— | | 98.5 | 100 |
| | | | | | | | 100 |
| 22 | 3 | O | O | n-pentyl | H | 245 | 100 |
| 23 | 3 | O | O | phenyl | H | 107 | 0 |
| 24 | 3 | O | O | 4-(trifluromethyl)phenyl | H | 85.9 | 0 |
| 25 | 3 | O | O | 2,4-difluorophenyl | H | 107 | 100 |
| | | | | | | | 100 |
| 26 | 3 | O | O | 2,4-dichlorophenyl | H | oil | |
| 27 | 3 | O | O | 3-(trifluromethyl)phenyl | H | oil | 0 |
| 28 | 3 | O | O | 2,2,3,3-tetrafluoropropyl | F | oil | |
| 29 | 3 | O | O | 2,2,2-trifluoroethyl | Cl | oil | |
| 30 | 3 | NH | O | 1,1,2,2-tetrafluoroethyl | H | 168–170 | 100 |
| 31 | 3 | NH | O | trifluoromethyl | H | 198–200 | 100 |
| | | | | | | | 100 |
| 32 | 3 | NH | O | 2,2,2-trifluoroethyl | H | 182 | 60 |
| 33 | 3 | NH | O | 2,2,2-trifluoroethyl | F | 193 | 100 |
| | | | | | | | 100 |
| 34 | 3 | NH | O | 2,2,3,3-tetrafluoropropyl | H | 135 | |
| 35 | 3 | NH | O | 2,2,2-trifluoro-1-methylethyl | H | 163–165 | |
| 36 | 3 | NH | O | 2,2,2-trifluoroethyl | Cl | 196 | |
| 37 | 3 | NH | O | ethyl | H | 179–181 | 0 |
| 38 | 3 | NH | O | i-propyl | H | 124–126 | 0 |
| 39 | 3 | NH | O | phenyl | H | 109–111 | 60 |
| 40 | 3 | NH | O | 2,4-difluorophenyl | H | 168 | 100 |
| | | | | | | | 100 |
| 41 | 3 | NH | O | 2-fluorophenyl | H | 192 | 100 |
| | | | | | | | 60 |
| 42 | 3 | NH | O | 2,4-dichlorophenyl | H | 115 | |
| 43 | 3 | NH | | Si(CH₃)₃ | H | 250 | |
| 44 | 4 | O | O | pentafluoroethyl | H | 70 | 100 |
| | | | | | | | 100 |
| | | | | | | | 100 |
| 45 | 4 | O | O | trifluoromethyl | H | 44–46 | 100 |
| | | | | | | | 97.5 |
| 46 | 4 | O | O | 2,2,2-trifluoroethyl | H | 80–83 | 100 |
| | | | | | | | 100 |
| | | | | | | | 100 |
| 47 | 4 | O | O | 2,2,2-trifluoroethyl | F | 73 | 100 |
| | | | | | | | 100 |
| 48 | 4 | O | O | 1,1,2,2-tetrafluoroethyl | H | 38–40 | 100 |
| | | | | | | | 100 |
| 49 | 4 | O | O | difluoromethyl | H | 67 | 100 |
| | | | | | | | 100 |
| 50 | 4 | O | O | 2,2,3,3-tetrafluoropropyl | H | 85 | |
| 51 | 4 | O | O | 2,2,2-trifluoro-1-methylethyl | H | oil | |
| 52 | 4 | O | O | n-propyl | H | 67–69 | 99 |
| | | | | | | | 100 |

-continued

| Example No. | Het | X | Y | R¹ | R² | MP °C. | Nematode Results at 12 ppm % control |
|---|---|---|---|---|---|---|---|
| | | | | | | | 90 |
| 53 | 4 | O | O | ethyl | H | 80–81 | 100 |
| | | | | | | | 100 |
| 54 | 4 | O | O | i-propyl | H | 61–66 | 100 |
| | | | | | | | 100 |
| 55 | 4 | O | O | t-butyl | H | 62–63 | 100 |
| | | | | | | | 100 |
| 56 | 4 | O | O | n-butyl | H | 56–58 | 0 |
| | | | | | | | 0 |
| 57 | 4 | O | O | 1-ethyl-1-methylpropyl | H | oil | 100 |
| | | | | | | | 97.5 |
| 58 | 4 | O | O | pentyl | H | oil | 100 |
| 59 | 4 | O | O | 4-(t-butyl)phenyl | H | oil | 0 |
| 60 | 4 | O | O | 4-(trifluoromethyl)-phenyl | H | 53–55 | 100 |
| | | | | | | | 90 |
| | | | | | | | 100 |
| | | | | | | | 100 |
| 61 | 4 | O | O | phenyl | H | oil | 100 |
| 62 | 4 | O | O | 2-fluorophenyl | H | oil | 95 |
| 63 | 4 | O | O | 2,4-difluorophenyl | H | 86 | 100 |
| | | | | | | | 100 |
| 64 | 4 | O | O | 4-chlorophenyl | H | 74 | 100 |
| 65 | 4 | O | O | 2,4-dichlorophenyl | H | 94 | |
| 66 | 4 | O | O | 4-cyanophenyl | H | 123–125 | |
| 67 | 4 | O | | —O—CF₂—O— | | | |
| 68 | 4 | O | S | 3-(trifluoromethyl)- | H | oil | |
| 69 | 4 | NH | O | 1,1,2,2-tetrafluoroethyl | H | 137–139 | 100 |
| | | | | | | | 100 |
| | | | | | | | 87.5 |
| | | | | | | | 100 |
| 70 | 4 | NH | O | trifluoromethyl | H | 115–117 | 100 |
| | | | | | | | 100 |
| 71 | 4 | NH | O | 2,2,2-trifluoroethyl | H | 156 | 100 |
| | | | | | | | 100 |
| 72 | 4 | NH | O | 2,2,3,3-tetrafluoropropyl | H | 138 | |
| 73 | 4 | NH | O | 2,2,2-trifluoro-1-methylethyl | H | 162–164 | |
| 74 | 4 | NH | O | 2,2,2-trifluoroethyl | Cl | | |
| 75 | 4 | NH | O | 2,2,2-trifluoroethyl | F | 136 | 100 |
| | | | | | | | 100 |
| 76 | 4 | NH | O | ethyl | H | 158–160 | 0 |
| 77 | 4 | NH | O | i-propyl | H | 185–187 | 0 |
| 78 | 4 | NH | O | 2-fluorophenyl | H | 146 | 100 |
| | | | | | | | 100 |
| 79 | 4 | NH | O | phenyl | H | 126–128 | 50 |
| 80 | 4 | NH | O | 2,4-difluorophenyl | H | 139 | 100 |
| | | | | | | | 100 |
| 81 | 4 | NH | O | 4-(trifluoromethyl)-phenyl | H | 137–139 | |
| 82 | 4 | NH | | Si(CH₃)₃ | H | | |
| 83 | 4 | O | O | difluoromethyl | H | 86 | 100 |
| | | | | | | | 100 |
| | | | | | | | 100 |
| 84 | 5 | O | O | 2,2,2-trifluoroethyl | H | 82–84 | 100 |
| | | | | | | | 100 |
| | | | | | | | 100 |
| | | | | | | | 100 |
| 85 | 5 | O | O | trifluoromethyl | H | 49–51 | 100 |
| | | | | | | | 100 |
| | | | | | | | 100 |
| 86 | 5 | O | O | 1,1,2,2-tetrafluoroethyl | H | 87–89 | 100 |
| | | | | | | | 100 |
| | | | | | | | 100 |
| 87 | 5 | O | O | 2,2,3,3-tetrafluoropropyl | H | 71 | |
| 88 | 5 | O | O | i-propyl | H | >40 | 100 |
| | | | | | | | 100 |
| 89 | 5 | O | O | t-butyl | H | 104–106 | 100 |
| | | | | | | | 99.5 |
| 90 | 5 | O | O | ethyl | H | 75–76 | 100 |
| | | | | | | | 40 |
| 91 | 5 | O | O | pentyl | H | 60–62 | 100 |
| | | | | | | | 100 |
| 92 | 5 | O | O | 3-(trifluoromethyl)-phenyl | H | oil | 100 |
| | | | | | | | 100 |
| 93 | 5 | O | O | phenyl | H | 100–102 | 100 |
| 94 | 5 | O | O | 4-(trifluoromethyl)- | H | 76–79 | 100 |

-continued

| Example No. | Het | X | Y | R¹ | R² | MP °C. | Nematode Results at 12 ppm % control |
|---|---|---|---|---|---|---|---|
| | | | | phenyl | | | 100 |
| | | | | | | | 100 |
| 95 | 5 | O | O | 2,4-difluorophenyl | H | 75–77 | |
| 96 | 5 | O | O | 4-chlorophenyl | H | 52 | |
| 97 | 5 | O | S | 3-(trifluoromethyl)-phenyl | H | 102 | |
| 98 | 5 | NH | O | 2,2,2-trifluoroethyl | H | 177.2 | 100 |
| | | | | | | | 100 |
| | | | | | | | 55 |
| 99 | 5 | NH | O | 2,2,2-trifluoroethyl | F | 174–178 | 100 |
| 100 | 5 | NH | O | 2,2,3,3-tetrafluoro-propyl | H | 121 | |
| 101 | 5 | NH | O | 2,2,2-trifluoro-1-methylethyl | H | 145 | |
| 102 | 5 | NH | O | i-propyl | H | 147–149 | 100 |
| | | | | | | | 95 |
| 103 | 5 | NH | O | 3-(trifluoromethyl)-phenyl | H | 134–136 | 0 |
| 104 | 5 | NH | O | phenyl | H | 134–136 | 100 |
| | | | | | | | 80 |
| | | | | | | | 80 |
| | | | | | | | 80 |
| 105 | 5 | NH | O | 2,4-difluorophenyl | H | 158 | |
| 106 | 5 | CH₂ | O | ethyl | H | oil | 100 |
| | | | | | | | 100 |
| | | | | | | | 100 |
| 107 | 6 | O | O | 2,2,2-trifluoroethyl | H | 101 | 0 |
| 108 | 6 | O | O | 4-(trifluoromethyl)-phenyl | H | 116 | 0 |
| 109 | 6 | NH | O | 2,2,2-trifluoroethyl | H | 150 | 0 |
| 110 | 7 | O | O | 4-(trifluoromethyl)-phenyl | H | 80–82 | 100 |
| 111 | 7 | NH | O | 2,2,2-trifluoroethyl | H | 151 | 100 |
| 112 | 7 | O | O | 2,2,2-trifluoroethyl | H | 85 | 100 |
| 113 | 7 | NH | O | 4-(trifluoromethyl)-phenyl | H | 218 | 100 |
| 114 | 8 | NH | O | 2,2,2-trifluoroethyl | H | 187 | 100 |
| 115 | 8 | O | O | 2,2,2-trifluoroethyl | H | 95 | 0 |
| 116 | 9 | O | O | 1,1,2,2-tetrafluoroethyl | H | 60–62 | 100 |
| | | | | | | | 100 |
| 117 | 9 | O | O | 2,2,2-trifluoroethyl | H | 109 | |
| 118 | 9 | O | O | 4-(trifluoromethyl)-phenyl | H | 95–97 | |
| 119 | 9 | NH | O | 2,2,2-trifluoroethyl | H | 217 | |
| 120 | 9 | NH | O | 2,2,3,3-tetrafluoro-propyl | H | | |
| 121 | 10 | O | O | pentafluoroethyl | H | 94–95 | 0 |
| 122 | 10 | O | O | ethyl | H | 87–88 | 0 |
| 123 | 10 | O | O | 4-(trifluoromethyl)-phenyl | H | 110–112 | 0 |
| 124 | 10 | O | O | phenyl | H | 110–112 | 60 |
| | | | | | | | 60 |
| 125 | 10 | NH | O | trifluoromethyl | H | 166–169 | 100 |
| | | | | | | | 80 |
| 126 | 10 | NH | O | ethyl | H | 174–176 | 0 |
| 127 | 11 | O | O | pentafluoroethyl | H | 79–80 | 100 |
| | | | | | | | 100 |
| 128 | 11 | O | O | 2,2,2-trifluoroethyl | H | 73–74 | 100 |
| 129 | 11 | O | O | difluoromethyl | H | | |
| 130 | 11 | O | O | n-butyl | H | | |
| 131 | 11 | O | O | 4-(trifluoromethyl)-phenyl | H | 106–108 | 100 |
| | | | | | | | 100 |
| | | | | | | | 100 |
| | | | | | | | 100 |
| 132 | 11 | O | O | 3-(trifluoromethyl)-phenyl | H | oil | 100 |
| | | | | | | | 100 |
| 133 | 11 | O | O | phenyl | H | 60 | 100 |
| | | | | | | | 100 |
| 134 | 11 | O | O | 4-chlorophenyl | H | 148–150 | |
| 135 | 11 | NH | O | trifluoromethyl | H | 243–249 | 0 |
| 136 | 11 | NH | O | ethyl | H | 220–222 | 0 |
| | | | | | | | 0 |
| 137 | 12 | NH | O | phenyl | H | | |
| 138 | 12 | NH | O | 2,2,2-trifluoroethyl | H | 84–85 | |
| 139 | 13 | NH | O | trifluoromethyl | H | 163–164 | 100 |
| | | | | | | | 100 |
| 140 | 13 | NH | O | 2,2,2-trifluoroethyl | H | 139–140 | 100 |
| 141 | 13 | NH | O | phenyl | H | 157–158 | 0 |

-continued

| Example No. | Het | X | Y | R¹ | R² | MP °C. | Nematode Results at 12 ppm % control |
|---|---|---|---|---|---|---|---|
| 142 | 14 | O | O | t-butyl | H | 75 | 99 |
|  |  |  |  |  |  |  | 97.5 |
|  |  |  |  |  |  |  | 90 |
| 143 | 14 | O | O | n-butyl | H | 60–61 | 100 |
| 144 | 14 | NH | O | ethyl | H | 164 | 0 |
| 145 | 15 | NH |  | Si(CH₃)₃ | H | 133–135 |  |
| 146 | 15 | NH | O | 1,1,2,2-tetrafluoroethyl | H | 153–155 | 100 |
|  |  |  |  |  |  |  | 45 |
| 147 | 15 | NH | O | 2,2,2-trifluoroethyl | H | 149–150 | 100 |
|  |  |  |  |  |  |  | 97.5 |
| 148 | 15 | O | O | 1,1,2,2-tetrafluoroethyl | H | 41–43 | 100 |
|  |  |  |  |  |  |  | 100 |
| 149 | 15 | O | O | 2,2,2-trifluorethyl | H | 74–76 | 100 |
|  |  |  |  |  |  |  | 100 |
| 150 | 15 | O | O | 3-(trifluoromethyl)-phenyl | H | 50–60 | 0 |
| 151 | 16 | NH | O | 1,1,2,2-tetrafluoroethyl | H | 145–147 | 100 |
|  |  |  |  |  |  |  | 100 |
|  |  |  |  |  |  |  | 25 |
|  |  |  |  |  |  |  | 100 |
| 152 | 16 | NH | O | 2,2,2-trifluoroethyl | H | 150–151 |  |
| 153 | 16 | NH | O | ethyl | H | 155–160 | 0 |
| 154 | 17 | O | O | pentafluoroethyl | H | 72–74 | 100 |
|  |  |  |  |  |  |  | 35 |
| 155 | 17 | NH | O | 2,2,2-trifluoroethyl | H | 165–166 | 0 |

The following Table II identifies specific compounds of formula (1) wherein Ar is a group of formula (19) and gives results of testing them in the above described peanut root knot nematode assay.

TABLE II

| Example No. | Het | X | Z | MP °C. | Nematode Results at 12 ppm % control |
|---|---|---|---|---|---|
| 156 | 2 | O | Cl | 106–107 | 0 |
| 157 | 2 | NH | F | 121–122 |  |
| 158 | 2 | NH | Cl | 162–163 |  |
| 159 | 3 | O | Cl | 139–140 | 0 |
| 160 | 3 | O | F | 126–127 |  |
| 161 | 3 | O | Br | 130 | 100 |
|  |  |  |  |  | 70 |
| 162 | 3 | NH | Br | 198–199 |  |
| 163 | 3 | NH | Cl | 176–177 | 0 |
| 164 | 3 | NH | I | 221–223 | 0 |
| 165 | 3 | CH₂ | Cl | 97 | 0 |
|  |  |  |  |  | 100 |
| 166 | 4 | O | Cl | 57–58 | 100 |
| 167 | 4 | O | Br | 64–65 | 100 |
| 168 | 4 | O | F | 93–94 |  |
| 169 | 4 | NH | Cl |  | 60 |
| 170 | 4 | NH | Br | 190–192 | 100 |
| 171 | 4 | NH | F | 171–173 |  |
| 172 | 5 | O | Cl | 85–87 | 100 |
| 173 | 5 | NH | Cl | 197–200 | 100 |
| 174 | 9 | O | Cl | 88–90 | 80 |
|  |  |  |  |  | 75 |
| 175 | 10 | NH | Cl | 178.5–180.5 |  |
| 176 | 11 | O | Cl | 126–128 |  |
| 1779 | 11 | NH | Cl | 271–275 | 0 |
| 178 | 12 | O | Cl | 86 | 0 |
| 179 | 13 | NH | Cl | 193–194 | 100 |
|  |  |  |  |  | 99.5 |
| 180 | 15 | NH | Cl | 189–190 | 0 |

The compounds of formula (1) are known compounds, or they are made using well known chemical procedures The required starting materials are commercially available, or they are readily synthesized using standard procedures. Compounds of formula (1) wherein Het is of formula (2) or (3) can be synthesized, for example, by the methods disclosed in U.S. Pat. No. 5,114,939, issued May 19, 1992, which is hereby incorporated herein by reference. Compounds wherein Het is of formula (4), (5), (6), (7), (8), or (9) can be synthesized, for example, by the methods disclosed in U.S. patent application Ser. No. 07/324,056, filed Mar. 16, 1989, (pending), corresponding to EPA 326329, which is hereby incorporated herein by reference, Compounds wherein Het is of formula (10), (11), (12), or (13) can be synthesized, for example, by the methods disclosed in U.S. Pat. No. 5,034,393, issued Jul. 23, 1991, which is hereby incorporated herein by reference. Compounds wherein Het is of formula (14) can be synthesized, for example, by the methods disclosed in U.S. patent application Ser. No. 07/502,364 filed Mar. 30, 1990, now U.S. Pat. No. 5,137,879 which is hereby incorporated herein by reference. Compounds wherein Het is of formula, (16), or (17) can be synthesized, for example, by the methods disclosed in U.S. patent application Ser. No. 07/502,342, filed Mar. 30, 1990, (pending), corresponding to EPA 452002 which is hereby incorporated herein by reference The method of this invention is practiced in accordance with standard techniques for the application of nematicides. In general, good nematicidal activity can be expected at rates of 1–10 lbs/acre.

The compounds of formula (1) are typically applied in the form of nematicide compositions which comprise a compound of formula (1) and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art.

Granular compositions usually contain from about 0.5% to about 15% by weight of the compound, dispersed in an inert carrier which consists entirely or in large part of clay or a similar inexpensive substance. Such compositions are usually prepared by dissolving the compound in a suitable solvent, and applying it to a granular carrier which has been preformed to the appropriate particle size, in the range of from about 0.5 to 3 mm. Such compositions may also be formulated by making a dough or paste of the carrier and compound, and crushing and drying to obtain the desired granular particle size. In use, granules are incorporated into the soil before planting, or applied in the furrow with the seed at planting, or applied in a band on top of a seed row, or broadcast and then incorporated into the soil, or used as a side dressing to an established crop.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound Nematicides are also applied as dispersions. For example they can be applied as aqueous drenches around growing plants or applied incrementally via an irrigation system. The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 50 to about 500 grams per liter of liquid, equivalent to about 5% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional non-ionic surfactants, such as those discussed above.

Aqueous suspensions comprise suspensions of water-insoluble compounds of this invention, dispersed in an aqueous vehicle at a concentration in the range from about 5% to about 50% by weight Suspensions are prepared by finely grinding the compound, and vigorously mixing it into a vehicle comprised of water and surfactants chosen from the same types discussed above Inert ingredients, such as inorganic salts and synthetic or natural gums, may also be added, to increase the density and viscosity of the aqueous vehicle It is often most effective to grind and mix the compound at the same time by preparing the aqueous mixture, and homogenizing it in an implement such as a sand mill, ball mill, or piston-type homogenizer.

When applied in the form of a dispersion of the active ingredient in a liquid carrier, it is conventional to refer to application rates in terms of the concentration of active ingredient in the carrier The most widely used carrier is water.

It is equally practical, when desirable for any reason, to apply the compound in the form of a solution in an appropriate organic solvent, usually a bland petroleum oil, such as the spray oils, which are widely used in agricultural chemistry.

The following formulations of compounds of the invention are typical of compositions useful in the practice of the present invention.

| A. 0.75 Emulsifiable Concentrate | |
|---|---|
| Compound of Formula (1) | 9.38% |
| "TOXIMUL D" | 2.50% |
| (nonionic/anionic surfactant blend) | |
| "TOXIMUL H" | 2.50% |
| (nonionic/anionic surfactant blend) | |
| "EXXON 200" | 85.62% |
| (naphthalenic solvent) | |
| B. 1.5 Emulsifiable Concentrate | |
| Compound of Formula (1) | 18.50% |
| "TOXIMUL D" | 2.50% |
| "TOXIMUL H" | 2.50% |
| "EXXON 200" | 76.50% |
| C. 1.0 Emulsifiable Concentrate | |
| Compound of Formula (1) | 12.50% |
| N-methylpyrrolidone | 25.00% |
| "TOXIMUL D" | 2.50% |
| "TOXIMUL H" | 2.50% |
| "EXXON 200" | 57.50% |
| D. 1.0 Aqueous Suspension | |
| Compound of Formula (1) | 12.00% |
| "PLURONIC P-103" | 1.50% |
| (block copolymer of propylene oxide and ethylene oxide, surfactant) | |
| "PROXEL GXL" | .05% |
| (biocide/preservative) | |
| "AF-100" | .20% |
| (silicon based antifoam agent) | |
| "REAX 88B" | 1.00% |
| (lignosulfonate dispersing agent) | |
| propylene glycol | 10.00% |
| veegum | .75% |
| xanthan | .25% |
| water | 74.25% |
| E. 1.0 Aqueous Suspension | |
| Compound of Formula (1) | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |
| F. 1.0 Aqueous Suspension | |
| Compound of Formula (1) | 12.50% |
| "MAKON 10" | 1.50% |
| "ZEOSYL 200" (silica) | 1.00% |
| "AF-100" | 0.20% |
| "POLYFON H" | 0.20% |
| (lignosulfonate dispersing agent) | |
| 2% xanthan hydrate | 10.00% |
| water | 74.60% |
| G. Wettable Powder | |
| Compound of Formula (1) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |
| H. Granules | |

| -continued | |
|---|---|
| Compound of Formula (1) | 5.0% |
| propylene glycol | 5.0% |
| Exxon 200 | 5.0% |
| Florex 30/60 granular clay | 85.0% |

We claim:

1. A method of inhibiting a nematode population which comprises applying to the locus of a nematode, a nematode inactivating amount of a compound of the formula (1):

$$Het-X-CH_2-CH_2-Ar \quad (1)$$

or an N-oxide or salt thereof, wherein

Het is a group selected from:

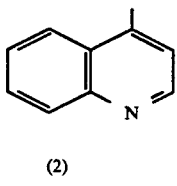 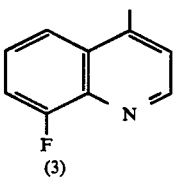

(2)　　　　　(3)

X is O, or NH;

Ar is a substituted phenyl group of formula (18), or (19).

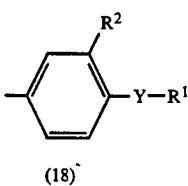 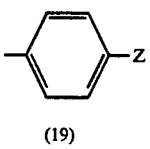

(18)　　　　　(19)

wherein

Y is O or S;

$R^1$ is $(C_2-C_5)$ alkyl, $(C_3-C_7)$ branched alkyl, halo $(C_1-C_4)$ alkyl, phenyl, or phenyl substituted with $CF_3$, CN or halo;

$R^2$ is H, F, or Cl, or $R^2$ combines with $Y-R^1$ to form $-CH_2-CH_2-O-$ or $-O-CF_2-O-$; and 2. A method of claim 1 wherein the compound of formula (1) being one that is able to provide at least 80% control when tested in the peanut root knot nematode assay at 12 ppm.

3. A method of claim 2 wherein the compound of formula (1) is one that is able to provide at least 80%. control when tested in the peanut root know nematode assay at 6 ppm.

4. A method of claim 1 wherein the Ar group is a substituted phenyl group of formula (18) wherein $R^1$ is halo $(C_1-C_4)$ alkyl.

5. A method of claim 4 wherein $R^1$ is selected from $CF_3$, $CHF_2$, $CF_2CF_3$, $CH_2CF_3$, $CF_2CHF_2$, $CH(CH_3)CF_3$, $CH_2CF_2CF_2H$, and $CH_2CF_2CF_3$.

6. A method of claim 1 wherein the Ar group is a substituted phenyl group of formula (18) wherein $R^1$ is a $(C_3-C_6)$ branched alkyl group.

7. A method of claim 1 wherein the Ar group is a substituted phenyl group of formula (18) wherein $R^1$ is a phenyl group that is monosubstituted with one halo or $CF_3$ group.

8. A method of claim 1 wherein the Ar group is a substituted phenyl group of formula (18) wherein $R^1$ is $(C_2-C_5)$ alkyl.

9. A method of claim 1 wherein the compound of formula (1) is one where the Het group is of formula (2), (3), (4), or (5).

10. A method of claim 10 wherein the Ar group is a substituted phenyl group of formula (16) wherein $R^1$ is halo $(C_1-C_4)$ alkyl.

11. A method of claim 11 wherein $R^1$ is fluoro $(C_1-C_4)$ alkyl.

12. A method of claim 11 wherein $R^1$ is selected from $CF_3$, $CHF_2$, $CF_2CF_3$, $CH_2CF_3$, $CF_2CHF_2$, $CH(CH_3)CF_3$, $CH_2CF_2CF_2H$, and $CH_2CF_2CF_3$.

13. A method of claim 10 wherein the Ar group is a substituted phenyl group of formula (16) wherein $R^1$ is a $(C_3-C_6)$ branched alkyl group.

14. A method of claim 9 wherein the Ar group is a substituted phenyl group of formula (18) wherein $R^1$ is a phenyl group that is monosubstituted with one halo or $CF_3$ group.

15. A method of claim 9 wherein the Ar group is a substituted phenyl group of formula (18) wherein $R^1$ is a $(C_2-C_5)$ alkyl.

16. A method of claim 1 wherein the compound of formula (1) is 8-fluoro-4-[2-[4-(pentafluoroethoxy)-phenyl]ethoxy]quinoline.

17. A method of claim 1 wherein the compound of formula (1) is 8-fluoro-4-[2-4-(t-butoxy)phenyl]ethoxy]-quinoline.

18. A method of claim 1 wherein the compound of formula (1) is 8-fluoro-4-[2-4-(n-pentoxy)phenyl]ethoxy]quinoline.

19. A method of claim 1 wherein the compound of formula (1) is 8-fluoro-4-[2-[3-fluoro-4-(2,2,2-trifluoroethoxy)-phenyl]ethoxy]quinoline.

20. A method of claim 1 wherein the compound of formula (1) is 8-fluoro-N-[2-[4-(trifluoromethoxy)-phenyl]ethyl]quinoline-4-amine.

* * * * *